(12) United States Patent
Ghisalberti

(10) Patent No.: US 7,371,396 B2
(45) Date of Patent: May 13, 2008

(54) DERMATOLOGICAL AND COSMETIC COMPOSITIONS

(75) Inventor: Carlo Ghisalberti, Sao Paulo (BR)

(73) Assignee: Relivia SRL, Milan (IT)

( * ) Notice: Subject to any disclaimer, the term of this patent is extended or adjusted under 35 U.S.C. 154(b) by 439 days.

(21) Appl. No.: 10/477,707

(22) PCT Filed: May 15, 2002

(86) PCT No.: PCT/IB02/01653

§ 371 (c)(1),
(2), (4) Date: Feb. 13, 2004

(87) PCT Pub. No.: WO02/092026

PCT Pub. Date: Nov. 21, 2002

(65) Prior Publication Data

US 2004/0127554 A1 Jul. 1, 2004

(30) Foreign Application Priority Data

May 17, 2001 (IT) ............ MI2001A1019

(51) Int. Cl.
*A61K 8/00* (2006.01)
*A61K 8/19* (2006.01)
*A61K 8/30* (2006.01)
*A61K 8/49* (2006.01)
*A61K 8/64* (2006.01)
*A61K 8/92* (2006.01)
*A61K 31/33* (2006.01)
*A61K 31/34* (2006.01)
*C07D 307/44* (2006.01)

(52) U.S. Cl. ............... 424/401; 514/461; 549/483
(58) Field of Classification Search ........ 424/401, 424/404, 59, 64, 70.6, 78.03; 514/844, 828, 514/861, 461; 549/497
See application file for complete search history.

(56) References Cited

U.S. PATENT DOCUMENTS

| | | | |
|---|---|---|---|
| 2,769,744 A * | 11/1956 | Usteri | ............ 514/461 |
| 2,918,412 A | 12/1959 | Wood | |
| 3,940,502 A * | 2/1976 | Winter et al. | ............ 426/536 |
| 3,987,189 A | 10/1976 | Gloxhuber et al. | |
| 5,780,042 A * | 7/1998 | Gers-Barlag et al. | ........ 424/401 |
| 6,022,530 A * | 2/2000 | Gers-Barlag et al. | ........ 424/59 |
| 6,060,041 A * | 5/2000 | Candau et al. | ........ 424/59 |
| 6,096,294 A * | 8/2000 | Hansenne et al. | ........ 424/59 |
| 6,552,050 B2 * | 4/2003 | Jacobson et al. | ........ 514/356 |
| 6,964,775 B1 * | 11/2005 | Wachter et al. | ........ 424/401 |
| 7,067,153 B2 * | 6/2006 | Grisoni | ........ 424/490 |
| 7,074,419 B2 * | 7/2006 | Dietz et al. | ........ 424/401 |
| 7,105,184 B2 * | 9/2006 | Pauly et al. | ........ 424/725 |
| 2002/0123517 A1 * | 9/2002 | Jacobson et al. | ........ 514/355 |
| 2003/0072725 A1 * | 4/2003 | Ley et al. | ........ 424/59 |
| 2004/0101508 A1 * | 5/2004 | Pauly et al. | ........ 424/74 |
| 2004/0147491 A1 * | 7/2004 | Jacobson et al. | ........ 514/150 |

FOREIGN PATENT DOCUMENTS

JP 2000-302642 * 10/2000

OTHER PUBLICATIONS

Computer English translation of detailed description of JP-2000-302642; retrieved on Dec. 16, 2005 from http://www.4.ipdl.ncipi.go.jp.*
Organic Chemistry, T.W. Graham Solomons, third Edition, John Wiley and Sons, New York, 1984, p. 795-796.*
Online Merck Manual Home Edition article on rosacea, accessed Jun. 6, 2006 (www.merck.com/mmhe/print/sec18/ch203/ch203k.html).*
Norris et al. "Fatty Acid Esters of Furfuryl Alcohol," Oil & Soap, Jul. 21, 1944, 193-196.*
Wikipedia online dictionary, (1) "Linseed Oil" and (2) "alpha-Linolenic acid," (1) en.wikipedia.org/wiki/Alpha-linolenic_acid and (2) en.wikipedia.org/wiki/Linseed_oil , respectively, both accessed on Dec. 4, 2006.*
Patent Abstracts of Japan; vol. 2000, No. 13, Feb. 5, 2001, & 2000 302642 A, Oct. 31, 2000.
Nemelka O. et al. Experimental survey of a new topical anti-oxidant based on Furfuryl palmitate in the treatment of child's and baby's dermatitis with eczema: results from a multicenter clinical investigation; Minerva Pediatr. 2002; 54:465-474 (Annex 2).
Nomeir AA, Silveira DM, McComish MF, Chadwick M., Drug Metab Dispos 20(2):198-204, 1992, abstract enclosed as Annex 4.

* cited by examiner

*Primary Examiner*—Johann R. Richter
*Assistant Examiner*—James H Alstrum-Acevedo
(74) *Attorney, Agent, or Firm*—Nixon & Vanderhye P.C.

(57) ABSTRACT

The present invention relates to a dermatological and/or cosmetic composition comprising a furfuryl derivative of formula (I), and its use in the treatment of dermatological disorders especially when caused by free radicals.

12 Claims, No Drawings

DERMATOLOGICAL AND COSMETIC COMPOSITIONS

This application is the U.S. national phase of international application PCT/IB02/0165300 filed 15 May 2002, which designated the U.S. PCT/IB02/01653 claims priority to IT Application No. MI2001 A001019 filed 17 May 2001. The entire contents of these applications are incorporated herein by reference.

FIELD OF THE INVENTION

The present invention relates to a dermatological and/or cosmetic composition comprising a furfuryl derivative and its use in the treatment of dermatological disorders especially when caused by free radicals.

BACKGROUND OF THE INVENTION

Specialists currently consider that a common cause of skin impairments, accelerated cellular aging and several dermatosis is the reduced defense and/or the overesponse to free radicals and subsequent oxidation phenomena.

Unfortunately the prevalence of dermatological disorders is increasing due to several environmental factors, possibly related to the oxidative stress, as described by Hallywell B in "Reactive oxygen species (ROS) in pathology with special reference to the skin" (Oxidative Stress in Dermatology—eds. Marcel Dekker Inc, New York, 3-11, 1993). Oxidative stress on skin may be prevented in different ways, as pointed out by Sies H in "Strategies of antioxidant defense" (Eur J. Biochem. 215: 213-219, 1993).

Exemplary, the atopic dermatitis (AT) is often the result of inherited sensitivities to an unknown allergen, most likely ROS, thereby manifested as redness, itching and oozing lesions that eventually scab over. This common inflammatory condition is spread out in young children and infants, more rarely appearing into adolescence and adulthood whilst, in some cases, the first symptoms show up later in life.

Singlet Oxygen ($^1O_2$) is an uncharged, low reactive ROS, whose characteristics allows its penetration and diffusion in the deep dermal layer and into cytoplasmatic fluids, where it may produce allergy and inflammation.

Beside accelerating skin-ageing, $^1O_2$ may produce dermatological disorders such as atopic dermatitis, psoriasis, allergic and inflammatory dermatitis, acne, rosacea and porphyria, erythemas, and so on.

The formation of $^1O_2$ is prompted by UV radiation and further promoted by p-amino benzoic acid (PABA) and others common UV-absorbers.

An efficient $^1O_2$ trap is furfuryl alcohol, a natural by-product quickly reacting with $^1O_2$ at room temperature by Diels-Alder cycloaddition, for example in tests carried out in an irradiated aqueous solutions PABA or photosensitizers and saturated with 02 (Allen J et al., in Chem. Res. Toxicol., 9, 3:605-609, 1996 and J Photochem Photobiol B, 32:1-2: 33-7, 1996; Kimel S et al., J Photochem Photobiol, 50. 2:175-83, 1989).

While furfuryl alcohol is an unstable chemical used in polymer manufacturing and in organic synthesis, some stable furfuryl alcohol derivatives occur as vegetal metabolites.

Simple furfuryl esters, such as furfuryl acetate, amylate and caprylate occur in trace amount in essential oil, being applied by the aroma industry for the manufacturing of flavor and fragrance compositions.

A furfuryl glicoside, namely furfuryl-I-beta-glucose, is the activator of (1-3)-beta-glucan synthase in higher plants, as found out by Callaghan, T. in Plant Physiol. 86, 1099-1103 (1988) and Ohana P. in J. Biol. Chem., 266(21): 13742-5 (1991).

A furfuryl nucleotide, namely kinetine (alias N6-furfuryladenine, furfuryladenine, or 6-furfuryl aminopurine), is a vegetal citokine with growth regulation role in plant cells, which has been applied as anti-iperproliferative and skin anti-ageing, as disclosed in U.S. Pat. No. 5,164,394 (Senetek, USA).

U.S. Pat. No. 5,13,594 discloses the topical use of 2,4-monofurfurylidene-sorbitol (furalglycitol), a synthetic furfural dichetal applied in cosmetic composition (Liktena™, UCB Corp.) with some results in the treatment of skin irritations.

However, furaglycitol tends to hydrolyze into sorbitol and furfural (furfurylaldehyde), which is at least twice as toxic as the furfuryl alcohol (Nomeir A A, Silveira D M, McComish M F, Chadwick M., Drug Metab Dispos 20(2):198-204, 1992). Hence, furalgycitol may not be recommended for chronic, repeated topical treatments.

Therefore, topical compositions comprising furfuryl derivatives capable of ameliorate the pro-inflammatory skin conditions on subjects over-responding to neutral ROS, which are furthermore easily applicable onto skin and displaying good tolerability and low toxicity, are still desired.

DESCRIPTION OF THE INVENTION

Surprisingly, there are no example of topical compositions comprising simple and stable furfuryl derivatives to treat dermatological disorders.

Accordingly, one object of the present invention is to provide a topical composition for the use on the skin that incorporate furfuryl derivatives as the active ingredient in the treatment of dermatological disorders, such as for example atopic dermatitis.

Therefore, the present invention provides a topical composition comprising, as an active ingredient a furfuryl derivative of formula (I):

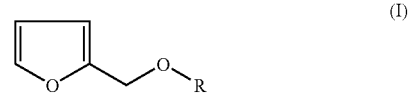

(I)

wherein R represents a linear or branched, saturated or unsaturated ($C_1$-$C_{32}$)-acyl or alkyl group, optionally substituted by ($C_1$-$C_8$)-alkoxy, carboxy, ($C_1$-$C_8$)-alkoxycarbonyl, amino, hydroxy, said amino and hydroxy being optionally ($C_1$-$C_{22}$)-acylated or ($C_1$-$C_{22}$)-alkylated; and salts or solvates thereof.

A particularly preferred composition of the invention is the one wherein R is a ($C_1$-$C_{32}$)-acyl group derived from a natural occurring fatty acid, more particularly When said fatty acid is a ($C_{12}$-$C_{18}$) fatty acid, advantageously when said fatty acid is the palmitoyl acid.

The topical composition of the invention is particularly useful in the treatment and/or prevention of dermatological disorders.

So, another object of the invention is the use of the composition of the invention for treating and/or preventing dermatological disorders.

The use of the furfuryl derivatives of formula (I) or of salts and solvates thereof for the manufacture of a topical medicament for treating and/or preventing dermatological disorders, is another object of the invention.

The use of the furfuryl derivatives of formula (I) or of salts and solvates thereof for the cosmetic treatment of the skin is a further object of the present invention.

A further object of the present invention is to provide a method for the treatment and/or prevention of dermatological disorders, more particularly those which are mentioned in the present application, which comprises administering to a mammal in need thereof an effective amount of a furfuryl derivative of formula (1) or a salt or solvate thereof.

The aforementioned furfuryl derivatives show high dermal compatibility and low irritation behavior when applied to human skin.

The present invention also provides an topical composition comprising the furfuryl derivative of formula (I) or a salt thereof in combination with a dermatologically acceptable carrier.

The expression "dermatologically acceptable" as used herein, means compatible with either or both of the skin and scalp.

The topical compositions of the present invention are effective in the fields of medicaments and cosmetics.

The topical compositions of the invention comprise a furfuryl derivative of formula (I), for example, in amounts of 0.01% to 10% by weight, preferably in amounts of 0.1% to 1% by weight, advantageously 0.2% to 0.5% by weight of the total weight of the composition.

The topical compositions according to the present invention are manufactured by known methods for example by mixing the furfuryl derivative with conventional dermatologically acceptable carriers, thus including bases for topical medicaments, cosmetics or hair-care products.

As set forth above, the topical compositions according to the present invention are particularly useful for treating a variety of skin dermatitis and diseases.

The composition of the invention are particularly indicated for the treatment of dermatological disorders.

Exemplary, non-limiting disorders include dermatitis conditions and skin impairments such as: atopic dermatitis, contact dermatitis, allergic contact dermatitis, allergic dermatitis, seborrheic dermatitis, nummular dermatitis, chronic dermatitis of hands and feet, generalized exfoliative dermatitis, stasis dermatitis, neonatal dermatitis, pediatric dermatitis, generalized exfoliative dermatitis; stasis dermatitis; localized scratch dermatitis, toxic/irritating contact eczema, allergic contact eczema, type I or type IV, photoallergic contact eczema, contact urticaria, dyshidrosiform eczema, age-caused wrinkles, sun damage and itching.

Other dermatological disorders which may be treated by the composition of the invention are:

Psoriasis: psoriasis vulgaris, flaking eczema, psoriasis pustulosa, psoriasis arthropatica, psoriatic erythroderma;

Rosacea;

Photodermatosis: radiodermatitis acuta and chronica (UV and ionizing radiation therapy), chronic actinic dermatitis, photourticaria (urticaria solaris), polymorphic photodermatosis and other polymorphic photodermatosis;

Prurigo: p. simplex acuta (strophulus, urticaria papulosa), subacuta, chronica;

Acne: acne vulgaris, juvenile and adult (acne with comedones, papulous, pustulous, nodose, i.e. nodular, nodulocystic acne), acne conglobata (special form: hidradenitis suppurativa), acne fulminans, acne tetrad, acne neonatorum, senile acne, mechanical acne forms (excoriated acne), acne cosmetica, folliculitis with superinfected acne (Staphylococci), occupation-related acne forms (for example chlorine acne);

Decubitus and Ulcus cruris;

Deficinent ipoactive skin: localized scratch dermatitis-rinophyma, ichthyosis, xerosis;

Perioral dermatitis.

Using routine methods, the topical compositions of the present invention may be formulated into a variety of preparations, depending on the intended use. These preparations include, but are not limited to, topical skin compositions for medical use, topical skin cosmetic compositions and hair-treatment compositions.

As topical skin compositions for medical use and topical skin cosmetic compositions, many types of ointments and lotion may be used.

The ointments may contain either an oil base or an emulsion base, including oil-in-water type and water-in-oil type emulsions. The oil base is not particularly critical, for example vegetable oils, animal oils, synthetic oils, fatty acids, and natural or synthetic glycerides are suitable.

When the topical compositions of the present invention are used as cosmetic compositions, the cosmetic acceptable ingredients may be optionally incorporated in arbitrary combinations as desired and determined in accordance with conventional skill in the art: oils, fats, waxes, surfactants, chelating agents, pH modifiers, preservatives, viscosity modifiers, colorants, preservatives, perfumes, dyestuffs, lower alkanols, etc.

The composition can contain humectants such as proteins or protein hydrolysates, amino acids, polyols, urea, allantoin, sugars and derivatives, water-soluble vitamins, plant extracts, hydroxyacids, polyols (e.g. glycerol), vitamins (e.g. D-panthenol), allantoin.

According to the invention, it is possible, inter alia, to combine furfuryl derivatives with other active agents intended in particular for the prevention and/or treatment of dermatological disorders.

Thus, another object of the invention relates to a composition comprising an effective amount of a furfuryl derivative of formula (I) along with one or more anti-oxidant substances active on neutral ROS such as $^1O_2$.

Among said antioxidants there may be mentioned carotenoid, flavonoids and plant polyphenols, nucleosides and azulenes.

Exemplary carotenoids includes all-trans-beta-carotene, alpha- gamma- and delta-carotene, docapreno- and dodecaprono-beta-carotene, lycopen, zaxanthin, astaxanthin, violaxanthin, lutein, bixin, canthaxnthin, cryptoxanthin. Exemplary flavonoids include taxifoline, catechin, epicatechin, eriodictyol, naringenin, rutin, troxerutin, chrysin, tangeretine, luteolin, opigallocatechin, epigallocatechin gallate, quercetin, fisetin, kaempferol, galangin, gallocatechin and epicatechin gallate. Exemplary plant polyophenols include gallic acid and esters thereof, caffeic acid, protocatechuic acid and ellagic acid. Exemplary nucleosides and derivatives include adenosine, guanosine, cytidine, thymidine and uridine, the corresponding deoxyribose derivatives, the nucleotides derived from the combination of a purine or pyrimidine base chosen from adenine, guanine, cytosine, thymine and uracile (abbreviated A, G, C, T, U) and a pentose (especially ribose and deoxyribose), the mono- di- or triphosphates, and especially 3'- and/or 5'-phosphates, as well an the oligonucleotides having for example up to 20 nucleotide units. Exemplary azulenes include azulene, camazulene, procamazulenes.

In the composition of the invention, the proportion by weight of product having a peroxidase activity capable of reducing organic peroxides may vary from 0.005% to 5%, and in particular from 0.01% to 3% by weight of the total composition.

A further object of the invention is a topical composition comprising an effective amount of furfuryl derivative of formula (I) in combination with one ore more other pharmaceutical active agents which are suitable for topical application.

Mention may be made, among these active agents, of, by way of example: agents which modulate cutaneous pigmentation and/or proliferation and/or differentiation, such as retinoic acid and its isomers, retinol and its esters, vitamin D and its derivatives, oestrogens, such as oestradiol, kojic acid or other withening agents; agents which modulate bacterial adhesion to the skin and/or mucous membranes, such as honey, in particular acacia honey, and certain sugar derivatives; agents for combating parasites, in particular metronidazole, crotamiton or pyrethroids; antifingals, in particular compounds belonging to the imidazole class, such as econazole, ketoconazole or miconazole or their salts, polyene compounds, such as amphotericin B, compounds of the allylamine family, such as terbinafine, or alternatively octopirox; antiviral agents, such as acyclovir; steroidal anti-inflammatory agents, such as hydrocortisone, betamethasone valerate, clobetasol propionate or non-steroidal anti-inflammatory agents, such as ibuprofen and its salts, diclofenac and its salts, acetylsalicylic acid, or acetaminophen; anaesthetic agents, such as lidocaine hydrochloride and its derivatives; antipruriginous agents, such as thenaldine, trimeprazine or cyproheptadine; keratolytic agents, such as alpha- and beta-hydroxycarboxylic acids or beta-ketocarboxylic acids, their salts, amides or esters and more particularly hydroxyacids, such as glycolic acid, lactic acid, salicylic acid, citric acid and generally fruit acids, and 5-(n-octanoyl)salicylic acid; agents for combating free radicals, such as alpha-tocopherol or its esters, superoxide dismutases, certain metal chelating agents or ascorbic acid and its esters; anti-seborrhoeics, such as progesterone; anti-dandruff agents, such as octopirox or zinc pyrithione; anti-acne agents, such as retinoic acid or benzoyl peroxide; substances such as substance P, CGRP or bradykinin antagonists or NO-synthase inhibitors, compounds described as being active in the treatment of sensitive skin and as exhibiting anti-irritant effects, in particular with respect to irritant compounds possibly present in the compositions.

Another object of the invention, is a topical composition comprising combination a furfuryl derivative of formula (I) in combination with one or more UV filters.

The UV filters can advantageously be used according to the invention, for example: 3-benzylidenecamphor derivatives, 4-aminobenzoic acid derivatives; esters of cynnamic acid, esters of salicylic acid, derivatives of benzophenone, esters of benzalmalonic acid, 2,4,6-trianilino-(p-carbo-2'-ethyl-1'-hexyloxy)-1,3,5-triazine, 2-phenylbenzimidazole-5-sulphonic acid and salts, sulfonic acid derivatives of benzophenones, sulfonic acid derivatives of 3-benzylidenecamphor, derivatives of dibenzoyhnethane (UVA fiters).

Cosmetic and/or dermatological compositions intended for light protection can also comprise inorganic pigments and physical UV-absorbers which are usually used in cosmetics, e.g. oxides of titanium, zinc, iron, zirconium, silicon, manganese, aluminum, cerium and mixtures thereof.

The UV filters which can be used in combination with the active compound according to the invention also include those in Section I of the Annex to 93/35/ECC article 5a.1 to the paragraph "U.V. absorbers", although this list is not intended to be limiting.

Moreover, we noticed that furfuryl derivatives wherein R is a benzoyl group or a higher alkyl and acyl group ($C \geqq 10$) displays low volatility and are highly compatible with the horny layer, hence they are more suitable as for the formulation on pharmaceutical and cosmetic composition for topical use.

The present invention is more specifically described and explained by means of the following Examples. It is to be understood that the present invention is not limited to those Examples, and may be made various changes and modifications without departing from the scope or spirit of the present invention.

The following examples are intended to illustrate the scope of the present invention but not to limit it.

EXAMPLE 1a

Synthesis of Furfuryl Palmitate 49 g of furfuryl alchol (0.5 mol) and 55.55 g of triethylamine (0.55 mol) in 500 ml $CH_2Cl_2$ were slowly added with 137.5 g of palmitoyl chloride (0.5 mol) while maintaining the temperature at 20° C. for 30 minutes under nitrogen athmosphere, then the reaction was heated to reflux for 20 minutes.

The reaction mixture is quenched with $H_2O$ (500 ml), and after stirring for 10 min, the aqueous phase was extracted with $CH_2Cl_2$ (2×300 ml). The organic phases were combined, washed with 10% HCl (200 ml), $H_2O$ (500 ml), saturated $NaHCO_3$ (300 ml), saturated NaCl (300 ml), dried ($MgSO_4$) and concentrated to provide whitish solid.

The solvent is distilled under vacuum to afford a beige fatty solid, which is recrystallized in ethanol under nitrogen to afford about 100 g of furfuryl palmitate as off-white powder, m.p. 31-33° C.

EXAMPLE 1b

Synthesis of Furfuryl Stearatate

The same procedure of Example 1a was applied with 0.5 moles of stearoyl chloride instead of palmitoyl chloride, to afford an off-white powder, m.p of 36-39° C.

EXAMPLE 1c

Synthesis of Furfuryl Emisuccinate

The same procedure of Example 1a was applied with 0.5 moles of succinic anhydride instead of palmitoyl chloride, to afford an off-white powder, m.p 32,7-36,4° C.

EXAMPLE 2

Test In Vivo With Atopic Dermatitis Subjects

Experiments were carried out on patients (n=20) of both sexes, of age above 18 years, suffering from severe disabling atopic dermatitis (AD) unresponsive to the current topical treatments.

All patients were subjected to complete blood count and measurements of renal and hepatic functions prior to treatment. Patients who had been systemically treated two months previously with corticoids, antibiotics, psoralenes and other immunosuppressants or with UV were excluded. Patients were supposed not to use any corticoid topically.

Material—A commercially available formulation Triderm Lenil (ICIM International srl, Gallarate, Italy) was used as such (formulation I) or with the addition of $1\times10^{-2}$ mol (0.33 g) of Furfuryl palmitate (formulation II).

Triderm Lenil ingredients: aqua, petrolatum, paraffinnum liquidum, dimethicone, laureth-9, C12-C15 alkyl benzoate, soy sterol, phenyl trimethicone, cetearyl alcohol, ribes nigrum, bisabolol, tocopheryl acetate, dimethicone copolyol, capryloyl glycine, glycyrrhetinc acid, superoxide dismutase, phytosphingosine, polyquaternium-7, sodium carbomer, hydroxypropyl guar, disodium EDTA, farnesol, sodium chloride.

Treatment—Out of 20 patients, 10 were included in the furfuryl palmitate-treated group (formulation I) and 10 in the control group (formulation I). The two groups were comparable as for sex, age, duration and severity of the eczema. Patients were divided in two groups and treated twice a day for one months either with the Furfuryl palmitate-containing cream or with the placebo cream (control group).

Evaluations—The progress of the disease was monitored with the SCORAD system (Dermatology 1993; 186: 23-31) drafted by European Task Force on Atopic Dermatitis (European Society of Pediatric Dermatology, Bordeaux, September 1990) with further modification by Hanifin and Rajka, thus by monitoring 3 criteria:

A) Lesione spread: analysis of surface involvement was performed during the clinical examination by drawing the involved areas on the evaluation sheet, then calculate the proportion of involved surface area segment by segment. For example, if ¾th of the right lower limb is interested by AD, the corresponding score is of about ⅞.

B) Grading of intensity: carried out in a chosen representative area in patients with localized lesions. In patients with areas varying in severity, a representative area of mean involvement is chosen. Dryness should be evaluated in a remote area of non-inflammatory skin. The elementary lesions were classified in the following manifestation: a) Erythema b) Edema/papulation c) Oozing/crusting d) Excoriation e) Lichenification, wherein each item is scored on a scale of 0 to 3, with the total for the intensity criteria is based on a maximum of 18

C) Subjective signs: by looking at the two most representative items concerning the quality of life of patients during the 3 previous days, i.e. pruritus and insomnia. The patient and/or one of his relatives expresses the intensity of pruritus or insomnia using a visual analog scale graded between 0 and 10.

SCORAD calculation is based on the following formula $A=$ SPREAD value/100

$B=$ INTENSITY value/18

$C=$ SUBJECTIVE SYMPTOMS value/20

SCORAD: $A/5+7\times B/2+C$

Results—Only in the furfuryl palmitate-treated subjects the mean of the values concerning the different clinical symptoms considered rapidly decreased from 57.0 (SEM 1.6 n=10) to 21.5 during the first two weeks of treatment. At the end of the treatment the 8 furfuryl palmitate-treated patients showed significant improvements of all the considered parameters, whereas two of them only showed improvements concerning skin scaling. No control subjects showed recovery signs. At the beginning of the treatment, the body area affected by eczema was 69% on the average in all patients. This gradually decreased during treatment, to reach 27% only in the furfuryl palmitate-treated patients. At the end of the treatment, the mean scores for itching decreased from 2.3 to 0.6 and for sleep disorders from 7.9 to 1.0. only in the furfuryl palmitate-treated patients.

EXAMPLE 3

O/W Cream 100 g of cream contain:

| | |
|---|---|
| Furfuryl palmitate | 0.3 g |
| Fluid paraffine | 2.0 g |
| Cethyl alcohol-(10)-POE | 4.0 g |
| Cetestearyl alcohol | 4.0 g |
| Triethanolamine | 1.75 g |
| Glycolic acid | 2.0 g |
| Butan-1,3-diol | 3.0 g |
| Xanthan gum | 0.3 g |
| Deionized water qb | to 100 g |

EXAMPLE 4

Alcoholic Lotion 100 g of an alcoholic lotion contain:

| | |
|---|---|
| Furfuryl adipate | 0.25 g |
| Tocoferyl acetate | 0.15 g |
| Glycolic acid | 4.0 g |
| Ethanol 95° | 40 g |
| Perfume | 0.3 g |
| Deionized water qb | a 100 g |

EXAMPLE 5

Cosmetic Anhydrous Preparation 100 g of a anhydrous composition contain:

| | |
|---|---|
| Furfuryl acetate | 0.2 g |
| Beta-carotene | 0.15 g |
| Silicone gum SE-30 (1) | 10 g |
| Fluid silicone 345 (2) | 18 g |
| Fluid silicone 344 (3) | 55.79 g |
| Borrage oil | 10.0 g |
| Cholesterol | 0.03 g |
| 2-Hydroxy-n-octanoic acid | 0.7 g |
| Ethanol 95° | 2.0 g |

(1) dimethylsilicone polymer with MW of around 50000 dalton and viscosity of 10000 centistokes at 25° C.
(2) cyclic dimethylsiloxane pentamer.
(3) dimethylsiloxane tetramer.

EXAMPLE 6

Lenitive Cream 100 g of cream contain:

| | |
|---|---|
| Furfuryl palmitate | 0.1 g |
| Stearin | 1.75 g |
| Propylenglycol monostearate | 2.7 g |
| Isopropyl lanolate | 3.5 g |
| Gel bentone of caprate and caprylate propylenglycol | 6.0 g |
| Isopropyl palmitate | 6.5 g |
| Silicone fluid 345 | 3.0 g |
| Sorbitan stearate | 1.8 g |
| PEO-Sorbitan stearate | 1.5 g |
| Cethyl alcol | 0.6 g |
| UVA and UVB filters | 2.0 g |
| Sodium edetate | 0.1 g |
| Aluminun silicate | 0.8 g |
| Carboxymethycellulose | 0.15 g |
| Propylenglycol | 4.0 g |
| Preservative | 0.5 g |
| Perfume | 0.35 g |
| Deionized water qb | to 100 g |

EXAMPLE 7

High Internal Phase W/O Emulsion 100 g of emulsion contain:

| | |
|---|---|
| Furfuryl palmitate | 0.3 g |
| Retynol | 0.5 g |
| Hydrogenated coconut oil | 5.9 g |
| Oleyl-(2)-POE | 5.0 g |
| Bentone 38 | 0.5 g |
| MgSO$_4$ 7H$_2$O | 0.3 g |
| Perfume | 0.2 g |
| Deionized water qb | to 100 g |

EXAMPLE 8

Anti-Sunburn Preparation 100 g of emulsion contain:

| | |
|---|---|
| Furfuryl palmitate | 0.3 g |
| Cyclomethycone | 2.0 g |
| Cethearyl alcohol + PEG-40 hydrogenated castor oil + Na cethearyl sulfate | 4.5 g |
| Octyl stearate | 3.0 g |
| Castor oil | 4.0 g |
| Glycerine | 3.0 g |
| Carbopol | 0.3 g |
| Idroxypropylmethylcellulose | 0.3 g |
| Octyl metoxycinnamate | 5.0 g |
| Butyl-methoxy-dibenzoyl methane | 0.5 g |
| Sodio edetate | 1.5 g |
| Perfume and preservative | q.s. |
| Acqua qb | to 100 |

EXAMPLE 9

Anti-Reddisch Cream 100 g of cream contain:

| | |
|---|---|
| Furfuryl acetate | 0.2 g |
| Beeswax | 1.5 g |
| Apricot kernel oil | 13.0 g |
| Preservatives | 0.3 g |
| Fragrance | 0.4 g |
| Trimethoxybenzene | 0.01 g |
| Xanthan | 0.5 g |
| Cyclopentadimethylsiloxane | 5.0 g |
| Sucrose mono- and dipalmitate/stearate | 3.0 g |
| Methylglucose sesquistearate | 3.0 g |
| Stearic acid | 1.0 g |
| Cetyl alcohol | 3.0 g |
| Deionized water qb | to 100 g |

The invention claimed is:

1. A topical composition comprising a furfuryl derivative having formula (I):

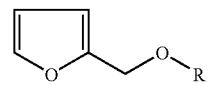

(I)

wherein:
R represents
   a linear or branched, saturated or unsaturated ($C_{10}$-$C_{32}$)-acyl group;
   a benzoyl group;
   a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or
   a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or ($C_1$-$C_{22}$)-alkylated;
   in admixture with a cosmetic or dermatological carrier, wherein the furfuryl derivative is present in an amount ranging from 0.01 to 10% by weight of the total composition.

2. The topical composition according to claim 1, wherein the furfuryl derivative is present in an amount ranging from 0.1 to 1% by weight of the total composition.

3. A topical composition in the form of a solution, a lotion, an emulsion, an oily-alcoholic or aqueous-alcoholic or alcoholic gel, a stick or an aerosol wherein the composition comprises a furfuryl derivative having formula (I):

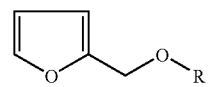

(I)

wherein:
R represents
   a linear or branched, saturated or unsaturated ($C_{10}$-$C_{32}$)-acyl group;
   a benzoyl group;

a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or ($C_1$-$C_{22}$)-alkylated;

in admixture with a cosmetic or dermatological carrier.

4. A topical composition comprising a furfuryl derivative having formula (I):

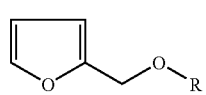

wherein:
R represents
a linear or branched, saturated or unsaturated ($C_{10}$-$C_{32}$)-acyl group;
a benzoyl group;
a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or
a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or ($C_1$-$C_{22}$)-alkylated;
in admixture with a cosmetic or dermatological carrier;
wherein the composition also comprises one or more agents selected from the group consisting of preservatives, bactericides, perfumes, anti-foaming agents, dyestuffs, pigments which have coloring properties, thickening agents, surface-active agents, emulsifiers, softening agents, moistening agents, humectant agents, fats, oils, waxes, alcohols, polyols, polymers, foam stabilizers, electrolytes, and organic solvents.

5. A topical composition comprising a furfuryl derivative having formula (I):

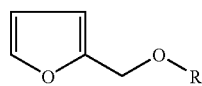

wherein:
R represents
a linear or branched, saturated or unsaturated ($C_{10}$-$C_{32}$)-acyl group;
a benzoyl group;
a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or
a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or ($C_1$-$C_{22}$)-alkylated;
in admixture with a cosmetic or dermatological carrier;
wherein the composition also comprises at least one agent selected from the group consisting of UV filters and inorganic pigments.

6. A topical composition comprising a furfuryl derivative having formula (I):

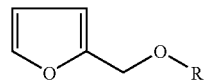

wherein:
R represents
a linear or branched, saturated or unsaturated ($C_{10}$-$C_{32}$)-acyl group;
a benzoyl group;
a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or
a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or ($C_1$-$C_{22}$)-alkylated;
in admixture with a cosmetic or dermatological carrier in combination with one or more anti-oxidant substances active on neutral ROS.

7. The topical composition according to claim 6 wherein said one or more anti-oxidant substances are selected iiifrom the group consisting of carotenoids, flavonoids, plant polyphenols, antioxidant enzymes, nucleosides and azulenes.

8. A topical composition comprising a furfuryl derivative having formula (I):

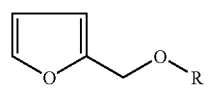

wherein:
R represents
a linear or branched, saturated or unsaturated ($C_{10}$-$C_{32}$)-acyl group;
a benzoyl group;
a linear or branched, saturated or unsaturated ($C_1$-$C_{32}$)-acyl group substituted with ($C_1$-$C_8$)-alkoxy, carboxy, amino, hydroxy, said amino and hydroxy groups being optionally ($C_1$-$C_{22}$)-acylated or ($C_1$-$C_{22}$)-alkylated; or
a ($C_1$-$C_{32}$)-alkyl group substituted with ($C_1$-$C_8$)-alkoxy, carboxy, ($C_1$-$C_8$)-alkoxycarbonyl, amino, hydroxy, said amino and hydroxy groups being optionally ($C_1$-$C_{22}$)-acylated or alkylated;

in admixture with a cosmetic or dermatological carrier in combination with one or more further pharmaceutical agents which are suitable for topical application.

9. A topical composition comprising a furfuryl derivative having formula (I):

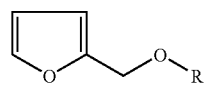

wherein:

R represents
- a linear or branched, saturated or unsaturated $(C_{10}-C_{32})$-acyl group;
- a benzoyl group;
- a linear or branched, saturated or unsaturated $(C_1-C_{32})$-acyl group substituted with $(C_1-C_8)$-alkoxy, carboxy, amino, hydroxy, said amino and hydroxy groups being optionally $(C_1-C_{22})$-acylated or $(C_1-C_{22})$-alkylated; or
- a $(C_1-C_{32})$-alkyl group substituted with $(C_1-C_8)$-alkoxy, carboxy, $(C_1-C_8)$-alkoxycarbonyl, amino, hydroxy, said amino and hydroxy groups being optionally $(C_1-C_{22})$-acylated or alkylated;

in admixture with a cosmetic or dermatological carrier;

in combination with one or more UV filters.

10. A method for the treatment of a dermatological disorder selected from the group consisting of atopic dermatitis, pediatric dermatitis, chronic dermatitis of the face, hands or feet in adults, contact dermatitis, allergic and irritant contact dermatitis, urticaria, photoallergic eczema, photodermatosis, solar erythema, sun damage, seborrheic dermatitis, and stasis dermatitis which comprises topically administering to a mammal in need thereof an effective amount of a furfuryl derivative having formula (I):

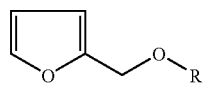

(I)

wherein:

R represents a linear or branched, saturated or unsaturated $(C_1-C_{32})$-acyl or alkyl in group, optionally substituted with $(C_1-C_8)$-alkoxy, carboxy, $(C_1-C_8)$-alkoxycarbonyl, amino, hydroxy, said amino and hydroxy being optionally $(C_1-C_{22})$-acylated or $(C_1-C_{22})$-alkylated.

11. A method for the cosmetic treatment of the skin which comprises topically administering to a mammal in need thereof an effective amount of a furfuryl derivative having formula (I):

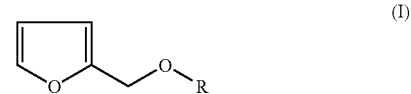

(I)

wherein:

R represents
- a linear or branched, saturated or unsaturated $(C_{10}-C_{32})$-acyl group;
- a benzoyl group;
- a linear or branched, saturated or unsaturated $(C_1-C_{32})$-acyl group substituted with $(C_1-C_8)$-alkoxy, carboxy, amino, hydroxy, said amino and hydroxy groups being optionally $(C_1-C_{22})$-acylated or $(C_1-C_{22})$-alkylated; or
- a $(C_1-C_{32})$-alkyl group substituted with $(C_1-C_8)$-alkoxy, carboxy, $(C_1-C_8)$-alkoxycarbonyl, amino, hydroxy, said amino and hydroxy groups being optionally $(C_1-C_{22})$-acylated or $(C_1-C_{22})$-alkylated;

in admixture with a cosmetic or dermatological carrer.

12. A method for the treatment of a dermatological disorder selected from the group consisting of atopic dermatitis, pediatric dermatitis, contact dermatitis, seborrheic dermatitis, allergic dermatitis, sunburn, eczema, itching and exfoliative dermatitis which comprises topically administering to a mammal in need thereof an effective amount of a furfuryl derivative having formula (I):

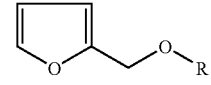

(I)

wherein:

R represents a linear or branched, saturated or unsaturated $(C_1-C_{32})$-acyl or alkyl in group, optionally substituted with $(C_1-C_8)$-alkoxy, carboxy, $(C_1-C_8)$-alkoxycarbonyl, amino, hydroxy, said amino and hydroxy being optionally $(C_1-C_{22})$-acylated or $(C_1-C_{22})$-alkylated.

* * * * *